(12) United States Patent
Fischer et al.

(10) Patent No.: US 6,676,919 B1
(45) Date of Patent: Jan. 13, 2004

(54) METHOD FOR PRODUCING PLATINUM METAL CATALYSTS

(75) Inventors: Martin Fischer, Ludwigshafen (DE); Markus Hölzle, Kirchheim (DE); Stefan Quaiser, Limburgerhof (DE); Achim Stammer, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,274

(22) PCT Filed: Apr. 6, 2000

(86) PCT No.: PCT/EP00/03086

§ 371 (c)(1),
(2), (4) Date: Oct. 4, 2001

(87) PCT Pub. No.: WO00/59635

PCT Pub. Date: Oct. 12, 2000

(30) Foreign Application Priority Data

Apr. 7, 1999 (DE) .......................................... 199 15 681

(51) Int. Cl.[7] .......................... C01B 15/01; B01J 23/40; B01J 23/44; C07C 5/03; C07C 5/10
(52) U.S. Cl. ...................... 423/584; 423/588; 502/325; 502/339; 568/799; 568/862; 585/266; 585/269; 585/270; 585/273; 585/274; 585/275; 585/276; 585/277
(58) Field of Search ................................ 502/325, 339; 423/584; 568/799, 862; 585/266, 269, 273, 275, 277, 270, 274, 276

(56) References Cited

U.S. PATENT DOCUMENTS

| 4,424,241 A | | 1/1984 | Abys |
| 5,250,490 A | * | 10/1993 | Ritscher et al. ............. 502/339 |
| 5,405,656 A | | 4/1995 | Ishikawa et al. |
| 5,505,921 A | * | 4/1996 | Lückoff et al. ............. 423/584 |
| 5,916,840 A | * | 6/1999 | Ebner et al. ................ 502/185 |
| 6,168,775 B1 | * | 1/2001 | Zhou et al. ................. 423/584 |
| 6,207,128 B1 | * | 3/2001 | Sellin et al. ................ 502/185 |

FOREIGN PATENT DOCUMENTS

| EP | 0 548 974 | 6/1993 |
| EP | 0 878 235 | 11/1998 |

* cited by examiner

*Primary Examiner*—Wayne A. Langel
(74) *Attorney, Agent, or Firm*—Oblon, Spivak, McClelland, Maier & Neustadt, P.C.

(57) ABSTRACT

The invention relates to a method for producing catalysts by immersion coating a metallic support with at least one platinum metal. An aqueous medium which comprises at least one platinum metal complex, at least one reduction agent and at least one complexer and which has a pH value of more than 4 is brought into contact with the metallic support in order to deposit the platinum metal, the platinum metal being deposited in the form of discreet, immobilised particles. The invention also relates to the catalysts obtained using this method and to their use for producing hydrogen peroxide and for hydrogenating organic compounds.

18 Claims, No Drawings

METHOD FOR PRODUCING PLATINUM METAL CATALYSTS

The present invention relates to a novel process for producing catalysts by electroless deposition of at least one platinum metal on a metallic support, the catalysts obtainable by this process, the use of the catalysts for the synthesis of hydrogen peroxide from the elements, for the hydrogenation of organic compounds and also a process for preparing hydrogen peroxide using these catalysts.

Catalysts comprising platinum metals as catalytically active substances are used in a wide variety of forms and are of great industrial importance, e.g. in the reduction or hydrogenation of organic compounds and in the catalytic purification of waste gases from industry and traffic.

For industrial applications, use is made wherever possible of supported platinum metal catalysts which contain only small amounts of the expensive noble metals on usually catalytically inactive support materials having a large surface area, e.g. carbon, aluminum oxide, silicon oxide, ceramic or other mineral supports.

Catalysts which are particularly easy to handle are ones in which the support can be used in the form of relatively large units, e.g. in the form of granules, beads or, in particular, woven meshes, gauzes or shaped bodies such as monoliths. Such supported catalysts are usually used as fixed-bed catalysts and make it possible to carry out catalytic processes in an economically advantageous continuous manner.

The application of the catalytically active metals to such porous supports is usually achieved by impregnating the support with solutions of salts or organometallic compounds of the catalytically active metal and subsequent immobilization by precipitation, hydrolysis, heat treatment, calcination and/or reduction. This usually necessitates repeated heating of the impregnated catalyst to from 200 to 1200° C. Thus, for example, DE-A-2 317 560 describes the production of a catalytic device by impregnation of a mineral monolith with a melt of trialkylaluminum at about 120° C., treatment with steam at 120° C./18 psi and subsequent firing at 400° C. The procedure is subsequently repeated using tetraalkylzirconium and the oxidic support obtained in this way is subsequently impregnated with a hexachloropalatinate, heated at 300° C. and activated.

Disadvantages of such porous catalysts are not only the complicated production method but also the low resistance toward strongly acidic reaction media. In addition, the use of such porous catalysts as fixed-bed catalysts usually leads to a severe, undesirable pressure drop in the reaction vessel.

In order to circumvent the abovementioned disadvantages, attempts have been made for some time to coat metallic supports with catalytically active metals, in particular platinum metals.

Metallic supports firstly have an increased stability and secondly metals can be worked to form thin sheets, wires, knitted meshes and gauzes which have a large surface area and favorable flow behavior. However, the application of the catalytically active metal to the metallic support is problematical. Thus, EP-A-0 198 435 discloses a process for producing catalysts in which the active components, e.g. noble metals, are vapor-deposited on the support. This process allows vapor deposition on metallic supports too, but the process is very complicated technically and requires expensive apparatuses. Furthermore, the process is not suitable for shaped catalyst bodies such as monoliths, wire mesh rings and helices.

Electrochemical plating processes or electroless plating processes, as are employed for finishing surfaces of materials, lead to smooth uniform coatings. The palladium-coated metals obtained are suitable, for example, as an inexpensive substitute for gold-coated metal parts in the electronics industry. However, substrates which have been coated in this way are unsuitable as catalysts.

Attempts have therefore been made to coat supports, including metallic supports, by impregnation with the catalytically active metal in soluble form. In order to obtain the porous surface necessary for impregnation, the surface of the metallic support is oxidized or, for example as described in EP-A-0 075 124, a porous oxide layer is applied to the metallic support and this is, as described above for porous nonmetallic supports, impregnated with the catalytically active metal. The catalysts obtained in this way display a good catalytic activity but are not suitable for many reactions in aggressive media because, particularly at low pH values, dissolution of the oxide layer and thus irreversible deactivation of the catalyst occurs.

A further method of producing supported noble metal catalysts on porous oxidic supports is the electroless deposition of noble metal salts from aqueous solutions by means of reducing agents in the presence of complexing agents such as ammonium chloride, EDTA or DTPA, as described in EP-A-0 878 235. In general, the porous support has to be activated by impregnation with sensitizers prior to the deposition process. Substances mentioned as suitable sensitizers are formaldehyde or aqueous solutions of silver nitrate, titanium salts or tin halides. The palladium catalysts produced by this method display good activity as hydrogenation: catalysts in the anthraquinone process for preparing $H_2O_2$ in an organic phase, but are, like most catalysts based on oxidic supports or coatings, not suitable for wet chemical processes in the presence of aggressive chemicals.

DE-A-196 42 770 discloses a process for preparing hydrogen peroxide by continuous reaction of hydrogen and oxygen over palladium catalysts in an aqueous or alcoholic medium. The metal-supported catalysts used in the examples are obtained by electroless deposition of Pd salts in a strongly acidic medium.

In "Catalysis of organic Reactions" (Scarrows and Prunier, editors), Marcel Dekker Inc., New York, 1995, pp. 115–124, J. R. Kosak describes the production of metal-supported noble metal catalysts and their use for the direct synthesis of $H_2O_2$ from hydrogen and oxygen. Here, the noble metal is applied to the metallic support by electroless plating using palladium chloride or palladium chloride and platinum chloride in the presence of sodium hypophosphite as reducing agent. The reduction of the noble metal takes place in strongly acidic solution in the presence of the support metal and leads to the formation of finely divided noble metal particles in the solution which becomes turbid and gray as a result. With increasing reaction time, the solution is decolorized to the extent that the noble metal deposits in the form of a black coating on the support.

In "Studies of Surface Science and Catalysis", Volume. 118, pp. 63–72, J. P. Reymond describes the production of metal-supported palladium catalysts and their use for the hydrogenation of acetophenones. The catalyst is produced by a method based on the work of Kosak, and here too palladium chloride is deposited in strongly acidic solution (pH <2.2) using sodium hypophosphite as reducing agent. Reymond, too, observes that the aqueous reaction medium becomes turbid and dark before commencement of the deposition of palladium on the metallic support, which Reymond attributes to the formation of very fine palladium particles in the aqueous medium. Reymond states that the formation of palladium particles in the solution and the deposition on the metallic support are processes which proceed simultaneously, with the formation of the particles in the aqueous medium proceeding more quickly than the deposition on the metal support. The fact that the catalysts produced in this way have a good catalytic activity compared to catalysts produced by conventional plating methods by means of deposition of noble metals from homogeneous solution leads Reymond to conclude that only the deposition of noble metals from a solution which has become inhomogeneous due to precipitated noble metal particles leads to catalytically active deposits on the metal supports.

A disadvantage of the catalysts produced by the methods of Kosak and Reymond is that the catalytically active coating obtained in this way has insufficient adhesion. The insufficient adhesion is reflected in the detachment of noble metal particles both when cleaning the catalyst after production and also during use in the catalytic process. This can lead to gradual deactivation of the catalyst and to contamination of the reaction medium with metal particles. Furthermore, activity and selectivity of the catalysts produced in this way are not satisfactory for an economical direct synthesis of $H_2O_2$ from hydrogen and oxygen, particularly when using hydrogen/oxygen mixtures below the explosive limit. The primary formation of metal particles in the liquid medium brings with it the risk of the suspended palladium not being completely deposited on the support and the particles frequently being attached very loosely to the metallic support It is therefore an object of the present invention to provide an improved process for producing metal-supported platinum metal catalysts which ensures very complete deposition of the expensive platinum metal and good adhesion of the noble metal to the metallic support. Furthermore, the catalysts should have a high catalytic activity and selectivity for the direct synthesis of $H_2O_2$ from hydrogen and oxygen. The catalysts should also have improved operating lives.

We have found that this object is achieved by a process for producing metal-supported catalysts, in which process an aqueous reduction solution which comprises at least one platinum metal complex, at least one reducing agent and a complexing agent and has a pH of greater than 4 is brought into contact with the metallic support to deposit the platinum metal, with the deposition of the platinum metal on the support surface occurring in the form of discrete, immobilized, i.e. firmly anchored, particles from the homogeneous, aqueous medium. The aqueous reaction medium is "homogeneous" for the purposes of the present invention when no turbidity or discoloration caused by precipitation of metal particles can be observed. Compared to the above-described prior art, no intermediate turbidity caused by precipitating metal particles is therefore observed when carrying out the coating process according to the present invention. The catalysts produced according to the present invention nevertheless have excellent catalyst properties, contrary to the assumption of Reymond (see above). Moreover, essentially quantitative deposition of the platinum metal from the solution can be achieved. The catalytic coatings produced according to the present invention surprisingly have a high abrasion resistance even in the case of great mechanical stress, for example as in the hydrogen peroxide synthesis due to a high throughput of circulating gas and high liquid circulation. Even after prolonged operation, no mechanical detachment is found.

In the process of the present invention, the deposition of the platinum metal is preferably carried out by an electroless method, i.e. not by electrochemical means but by addition of a reducing agent to the solution.

For the purposes of the present invention, platinum metals are the noble metals of transition group VIII of the Periodic Table, namely rhodium, ruthenium, palladium, osmium, iridium and platinum. Preference is given to ruthenium, rhodium, palladium and platinum, and particular preference is given to palladium and platinum. The catalysts of the present invention can comprise a plurality of platinum metals. Here, all combinations of the platinum metals mentioned are conceivable; preference is given to combinations of palladium and platinum, of palladium and rhodium, of palladium and iridium, of palladium, platinum and rhodium and of palladium, platinum and iridium. The particularly preferred combination is palladium and platinum. In the combinations comprising palladium, palladium preferably represents the main platinum metal component. The proportion of palladium is then preferably above 40% by weight, preferably above 60% by weight and particularly preferably above 80% by weight, based on the total platinum metal content. The further platinum metals which may be present as secondary constituents can in each case contribute up to 30% by weight, preferably up to 20% by weight and particularly preferably up to 15% by weight, of the total platinum metal content. The platinum metals preferably comprise from 80 to 100% by weight of palladium and from 0 to 20% by weight of platinum or iridium. In most cases, from 1 to 3 of the platinum metals specified make up more than 95% by weight of the amount of platinum metals used. If a main platinum metal is augmented by further platinum metals, the latter are generally present in amounts of greater than 0.001% by weight, preferably greater than 0.01% by weight, e.g. in an amount of about 0.1% by weight, about 1% by weight or about 5% by weight.

The catalytically active component may comprise not only platinum metals but also further elements as additional components or impurities. Additional components which can influence the activity and/or selectivity of the catalyst are, for example, metals such as cobalt, nickel, copper, silver, gold, chromium, molybdenum, tungsten, manganese, rhenium, aluminum, tin, lead, arsenic, antimony and bismuth, and nonmetals such as boron, carbon, silicon, nitrogen and phosphorus. The metals and nonmetals mentioned may be present either in ionic form or in nonionic form in the catalytically active coating. Furthermore, the catalytically active component may comprise further elements (metals and nonmetals) as impurities, e.g. as a result of the catalytically active components used containing impurities, or as a result of constituents of the components used in the process of the present invention being incorporated into the platinum metal coatings during the production of the catalysts of the present invention, e.g. alkali metals and alkaline earth metals, phosphorus, boron and halogens.

The additional components can be present in amounts of from 0.001 to 25% by weight, based on the platinum metal content. Additional components used as promoters or dopants are generally present in amounts of from 0.01 to 20% by weight, preferably from 0.1 to 15% by weight and in particular from 0.5 to 10% by weight, based on the platinum content.

In the process of the present invention, the platinum metals are preferably used as platinum metal complexes. Preference is given to using platinum metal complexes in which the platinum metal is present in the oxidation states +1 to +4. Complexes having a coordination number of four are preferred.

The process of the present invention is eminently suitable for producing platinum metal catalysts in which palladium is the main platinum metal component.

To product catalysts comprising palladium, in particular catalysts comprising palladium as main platinum metal component, palladium(II) complexes are preferred. Palladium(II) complexes in which palladium has a coordination number 4 are particularly useful.

Preference is is given to combinations of platinum metal ions and ligand whose complex formation constant is >1000 and in particular >10,000.

Suitable combinations of ligands and counterions for palladium complexes and for platinum metal complexes other than those of palladium can also be chosen subject to the fundamental principle of charge neutrality. Suitable negatively charged ligands are, for example, selected from among halides and pseudohalides, e.g. fluoride, chloride, bromide, iodide, CN, OCN and SCN, $C_1$–$C_6$-carboxylic acids such as formic acid, acetic acid and propionic acid and their salts, chelating ligands such as ethylenediaminetetraacetic acid (EDTA), nitrilotriacetic acid, 1,2-diaminocyclohexanetetraacetic acid and their salts, aminophosphonic acids such as nitrilomethylenephosphonic acid, diketonates such as acetylacetonate, hydroxycarboxylic acids such as glycolic acid, lactic acid, tartaric acid and gluconic acid and their salts. Suitable electrically neutral ligands are, for example, alkyl nitriles such as acetonitrile, amines such as ammonia, primary, secondary and tertiary $C_1$–$C_6$-alkylamines such as ethylamine, n-propylamine, isopropylamine, n-butylamine, tert-butylamine, hexylamine, dimethylamine, diethylamine, diisopropylamine, di-n-butylamine, trimethylamine, triethylamine, tripropylamine, N,N-dimethylethylamine, N,N-dimethyliso-propylamine and N,N-dimethylbutylamine, diamines, triamines, tetramines and polyamines such as ethylenediamine, diethylenetriamine and triethylenetetramine, nonaromatic and aromatic cyclic amines such as pyrrolidine, piperidine, morpholine, piperazine, pyrrole and their n-$C_1$–$C_6$-alkyl derivatives, pyridine and phenanthroline, phosphines such as phosphine, trimeric, secondary and tertiary $C_1$–$C_6$-alkylphosphines and $C_6$–$C_{12}$-arylphosphines, in particular triphenylphosphine, and sulfides such as $C_1$–$C_6$-monoalkyl and -dialkyl sulfides, $C_6$–$C_{12}$-monoaryl and -diaryl sulfides and oxygen compounds, di-$C_1$–$C_6$-alkanols and phenols and also their ethers.

Particularly preferred complexing ligands are the halides chloride and bromide; amines, in particular ammonia and triethylamine, cyanide and ethylenediaminetetraacetic acid, and also the di-, tri- or tetra-alkali metal (e.g. sodium) or ammonium salts thereof. Preferred counterions are alkali metals such as lithium, sodium and potassium, alkaline earth metals such as magnesium and calcium, nitrite, nitrate and ammonium.

Suitable platinum metal complexes preferably have a solubility of at least 0.01% by weight in water at room temperature (25° C.). The platinum metal complex(es) are, according to the present invention, used in an aqueous medium and are used in such a concentration that the platinum metal content of the solution is in the range from 0.01 to 20.0 g/l, preferably in the range from 0.1 to 2.0 g/l and particularly preferably in the range from 0.15 to 1.0 g/l, for example in the range from 0.15 to 0.25 g/l, from 0.2 to 0.5 g/l or from 0.35 to 0.8 g/l.

Preferred palladium complexes are $H_2PdHal_4$, $M_2PdHal_4$, $M_2Pd(CN)_4$, $(NH_4)_2PdHal_4$, $Pd(NH_3)_4Hal_2$, $Pd(NH_3)_4(NO_3)_2$ and $Pd(NH_3)_4(CH)_2$, where M is an alkaline metal, in particular sodium and potassium, and Hal is a halogen atom, in particular chlorine, bromine or iodine.

Further preferred platinum metal complexes are $(NH_4)_2IrCl_6$, $H_2PtCl_4$, $(NH_4)_2PtCl_4$, $Na_2PtCl_4$ and $K_2PtCl_4$.

In addition, the aqueous medium comprises at least one reducing agent in completely or partially dissolved form. Suitable. reducing agents are all substances or mixtures whose redox potential is below the redox potential of the platinum metal complex used, i.e. substances having a standard potential in aqueous medium of less than +0.5 volt, preferably a standard potential of less than 0 volt. The reducing agent or reducing agent mixture has a solubility of at least 1% by weight, preferably at least 10% by weight, in the aqueous medium at room temperature (25° C.). In preferred embodiments of the present invention, the reducing agent or the reducing agent mixture is virtually completely soluble in the aqueous medium.

Examples of suitable reducing agents are carboxylic acids such as formic acid, citric acid, lactic acid, tartaric acid and in particular the salts of carboxylic acids, preferably the alkali metal, alkaline earth metal, ammonium and $C_1$–$C_{10}$-alkylammonium salts, phosphorous or hypophosphorous acid, salts of phosphorous or hypophosphorous acid, in particular the alkali metal or alkaline earth metal salts, $C_1$–$C_{10}$-alkanols such as methanol, ethanol, and isopropanol, sugars such as aldoses and ketoses in the form of monosaccharides, disaccharides and oligosaccharides, in particular glucose, fructose and lactose, aldehydes such as formaldehyde, boron-hydrogen compounds or borohydrides, e.g. boranes, metal boranates and borane complexes, e.g. diborane, sodium borohydride and aminoboranes, in particular trimethylaminoborane, hydrazine and alkylhyradzines such as methylhydrazine, hydrogendithionites and dithionites, in particular sodium and potassium hydrogendithionite, sodium, potassium and zinc dithionite, hydrogensulfites and sulfites, in particular sodium and potassium hydrogensulfite, sodium, potassium and calcium sulfite, hydroxylamine and urea, and also mixtures thereof.

Preferred reducing agents are sodium hypophosphite and potassium hypophosphite, ammonium formate, trimethylamine-borane, sodium borohydride, sodium dithionite and sodium hydrogendithionite, and also mixtures of ammonium formate and sodium hypophosphite.

In general, at least one redox equivalent, based on the sum of the platinum metals and additional components (e.g. promoters/dopants), of reducing agent is used. The reducing agent is preferably used in excess. Particularly suitable molar ratios of reducing agent to platinum metal are in the range from 10:1 to 100:1, particularly preferably from 20:1 to 60:1, for example about 30:1, about 40:1 or about 50:1.

The electroless deposition of the platinum metal is advantageously carried out at a pH of the aqueous medium of greater than 4, preferably greater than 6, for example from 7 to 14, in particular from 8 to 12. It is generally necessary to add at least one base to the aqueous medium comprising the platinum metal complex and the reducing agent in order to obtain the desired pH. For the purposes of the present invention, bases are all substances or compounds which are suitable for adjusting the pH of the aqueous medium to the desired value. In particular, use is made of bases which have complex-stabilizing properties, i.e. have at least partial Lewis base character. The base is preferably selected from among metal oxides, metal hydroxides, in particular alkali metal hydroxides such as sodium hydroxide and potassium hydroxide, metal carbonates, in particular alkali metal and alkaline earth metal carbonates such as lithium carbonate, sodium carbonate, potassium carbonate, magnesium carbonate and calcium carbonate, nitrogen bases, in particular ammonia, primary, secondary and tertiary amines as described above in the discussion of the nitrogen-containing complexing ligands. Buffer systems, particularly those comprising the abovementioned bases, the salts of the abovementioned bases and/or suitable acids, are also suitable. Particularly preferred bases are ammonia and aqueous sodium hydroxide solution.

For the purposes of the present invention, aqueous media are substances or mixtures which are liquid under the process conditions and contain at least 10% by weight, preferably at least 30% by weight and in particular at least 50% by weight, of water. The part which is not water is preferably selected from among inorganic or organic substances which are at least partially soluble in water or at least partially miscible with water. For example, the substances which are different from water are selected from among organic solvents, $C_1$–$C_{22}$-alkanols, in particular methanol, ethanol, n-propanol, isopropanol, n-butanol, sec-butanol, tert-butanol, pentanols and hexanols, $C_4$–$C_8$-cycloalkyl ethers such as tetrahydrofurans, pyrans, dioxanes and trioxanes, $C_1$–$C_{12}$-dialkyl ethers such as dimethyl ether, dibutyl ether and methyl butyl ether, and customary auxiliaries as are used in processes for electroless deposition.

The aqueous medium preferably contains less than 40%, in particular less than 30% and particularly preferably less than 20%, of organic solvent.

In preferred embodiments of the process of the present invention, the aqueous medium is essentially free of organic solvents.

Apart from the platinum metal complex, the reducing agent and the base, the aqueous solution further comprises at least one complexing agent, preferably containing at least one halogen, nitrogen, oxygen and/or phosphorus atom. For the purposes of the present invention, complexing agents are ions or compounds which are able to stabilize metal ions in aqueous media. In general, such complexing agents are donors or salts of donors. Suitable donors generally have a free electron pair which can interact with the metal ions. Complexing agents which are particularly suitable for the process of the present invention are those which contain the abovementioned heteroatoms as donors. Examples of suitable complexing agents are the metal salts, in particular the alkali metal and alkaline earth metal salts, of the compounds mentioned above as complexing ligands for the platinum metals.

Particularly useful complexing agents are hydrohalic acids such as hydrogen bromide, hydrogen chloride and hydrogen iodide, the metal salts of the hydrohalic acids mentioned, in particular the alkali metal and alkaline earth metal salts, and also tin dihalides, zinc dihalides, ammonium salts such as ammonium chloride, ammonium bromide, ammonium iodide, ammonium nitrite, ammonium nitrate, the alkali metal, alkaline earth metal and ammonium salts of carboxylic acids and hydroxycarboxylic acids, e.g. sodium and/or potassium tartrate.

In general, platinum metal complex, reducing agent, base and complexing agent can be added to the aqueous medium in any order. Preferably, at least part of the base is added to the aqueous medium before the reducing agent is added.

In one embodiment of the process of the present invention, the platinum metal complex and if desired the complexing agent and/or the base is/are first added to the aqueous medium and the reducing agent is subsequently added.

In general, the process of the present invention is carried out at temperatures in the range from 0 to 100° C., preferably in the range from 30 to 100° C. and in particular in the range from 40 to 85° C.

For the purposes of the present invention, metallic supports are preferably bodies which have essentially solid metal (i.e. in the oxidation state 0) on at least the (outer) surface which can be reached by the reaction medium. Suitable metals for the metallic supports are all metals and alloys which have sufficient stability under the production conditions of the platinum metal catalysts of the present invention and/or under the use conditions of the catalysts produced therewith. Suitable metals are, for example, magnesium, aluminum, titanium, vanadium, chromium, molybdenum, tungsten, iron, cobalt, nickel, copper, silver and zinc and also mixtures and alloys thereof. As further alloying constituents or secondary constituents, it is possible for elements such as the nonmetals boron, carbon, nitrogen, oxygen, silicon, phosphorus, sulfur and further transition metals to be present. In general, the further alloying constituents or secondary constituents, with the exception of carbon, are present in a proportion of less than 20% by weight, preferably less than 15% by weight and in particular less than 5% by weight, per element, based on the total weight of the metallic support. Carbon can be present in the metallic supports in amounts of up to 25% by weight. If the metallic supports comprise further alloying constituents or secondary constituents, these further constituents are generally present in amounts of at least 0.01% by weight and preferably about 0.1% by weight, based on the total weight of the metallic support. The metallic support preferably consists essentially of steel or iron, copper, aluminum, silver, nickel, chromium, tungsten, titanium or a mixture and/or alloy thereof. Preference is given to high-alloy stainless steels or metals which are protected against further corrosion by formation of a passivating layer, for example chromium steels, chromium-nickel steels, chromium-nickel-titanium steels and chromium-nickel-molybdenum steels, V4A steels and heat-resistant steels having the material numbers 1.4539, 1.4571, 1.4016, 1.4767, 1.4401, 2.4610, 1.4765, 1.4847, 1.4301 and 1.4742, and also alloys such as Monel and Hastelloy.

The metallic supports can be used directly as sheets, perforated sheets, grids, wires or preferably as wire meshes, woven or knitted meshes and in particular in the form of shaped bodies. Shaped bodies for the purposes of the invention are preferably three-dimensional bodies made of the above-described supports which can be formed, for example, by rolling, bending, pressing and the like, for example packing elements such as Raschig rings, saddles, Pall® rings, wire spirals, wire mesh rings, with or without web, and monoliths. For the purposes of the present invention, monoliths are shaped bodies in the form of ordered packings which are installed in the reactor and, owing to many flow channels, have a large surface area per unit volume. Preferred shaped bodies have channels with hydraulic radii (for definition, see VDI-Wärmeatlas, Section LE 1), in the range from 0.1 to 10 mm. Woven meshes having different types of weave can be produced from wires and fibers of the abovementioned metals and materials, for example plain weaves, twills, braids, five-shaft Atlas weaves and other. special weaves. These woven meshes are preferably combined to form multilayer woven composites. Suitable monolithic catalyst supports based on woven meshes are described in EP-A-198 435. Other suitable support bodies are metal foams and metal sponges, in particular open-celled or open-pored metal foams or sponges.

Particularly suitable monoliths are built up of a plurality of layers of corrugated, creased and/or smooth woven meshes which are arranged so that adjacent layers form more or less closed channels. The hydraulic diameter of the channels is preferably in the range from 1 to 10 mm, in particular from 1.5 to 3 mm (as per the definition in VDI-W ärmeatlas, Section LE 1). The channels can be straight or curved. Preference is given to using multilayer meshes in which smooth and corrugated or creased woven meshes alternate. Monoliths in which the woven meshes are partly or completely replaced by sheets, knitted meshes or expanded metal can likewise be used. While packing elements are generally introduced into the reactor as a random bed, monoliths are preferably installed in the reactor, in particular so that the channels are inclined to the flow direction of the reaction medium. The layers of woven mesh themselves are preferably installed parallel to the flow direction in the reactor. If a plurality of these structural units are arranged in succession, they are preferably installed so that the flow channels are alternately inclined in opposite directions to the flow direction. The structural units are preferably installed so that the layers of woven mesh of two successive structural units have an angle to one another of preferably about 90°. Wound modules of corrugated or creased and possibly also smooth layers of woven mesh are likewise suitable.

The deposition of the catalytically active component, i.e. the platinum metals and possibly promoters and/or the dopants can be carried out before or after the metallic supports have been formed into shaped bodies. The deposition of the catalytically active components is preferably carried out after forming into shaped bodies. When shaping the bodies and/or installing them in the reactor, care has to be taken to ensure that as large as possible a proportion of the surface area of the catalyst is readily accessible to the flowing reactants and that the pressure drop in the reactor is as low as possible. This is particularly important in processes using liquid reaction media.

Suitable metallic supports have not only sufficient mechanical strength but also preferably have a geometric surface area of greater than 0.5 m²/l, in particular greater than 1.5 m²/l and preferably greater than 2.5 m²/l.

Before application of the platinum metal to the metallic support, the latter is preferably cleaned thoroughly, e.g. by treatment with aqueous surfactant solutions and/or electrolyte salt solutions as are customary in electroplating, and/or by treatment with organic solvents such as ethyl acetate, acetone and water, if desired with the assistance of ultrasound. The metallic support can advantageously be subjected to a surface treatment prior to deposition of the platinum metal so as to increase the surface area of the metallic support and/or improve the adhesion of the platinum metal to the support, for example partial dissolution of the surface of the support by means of acids such as hydrohalic acids, in particular hydrochloric acid and hydrobromic acid, nitric acid, sulfuric acid, phosphoric acid and mixtures thereof. The partial dissolution of the surface is preferably carried out so that from 0.1 to 15% by weight, preferably from 1 to 5% by weight, of the support is dissolved.

The active components, i.e. the platinum metal or the platinum metals and any additional components present, generally make up from $5 \times 10^{-4}$ to 5% by weight, in particular from $10^{-3}$ to 1% by weight, particularly preferably from 0.1 to 1.0% by weight, based on the total mass of the catalyst (support+catalytically active coating).

If an additional complexing agent is added to the solution, it is generally used in an amount of from 0.1 to 10,000 equivalents, preferably from 1 to 1000 equivalents, particularly preferably from 10 to 600 equivalents, of the complexing agent, based on the platinum metal component.

For example, the metallic support is first brought into contact with the aqueous medium when the aqueous medium contains at least the platinum metal complex, the reducing agent, at least part of the base and, if desired, the additional complexing agent. The aqueous medium preferably contains all components used in the electroless deposition before the aqueous medium is brought into contact with the metallic support. Likewise, the support can be initially brought into contact with all abovementioned components apart from the platinum metal. The platinum metal is then added at the reaction temperature or a temperature which is, for example, up to 30° C. lower. For the purposes of the present invention, the "reaction temperature" is the temperature at which the deposition of the platinum metal particles on the support occurs.

The deposition of noble metals on metallic supports is known from the prior art as electroplating or electroless plating. In these processes, the formation of a thin, pore-free, smooth layer, i.e. a pore-free smooth film, on the support is sought. Such smooth layers are required, for example, for electric contacts for, for example, printed circuits and membranes. A supported palladium catalyst produced by a typical plating method displays only a low activity in the formation of hydrogen peroxide from hydrogen and oxygen.

The catalysts of the present invention differ fundamentally from coated metallic supports produced by plating methods, although some or all of the chemicals used for the electroless deposition of the noble metal according to the present invention can be the same ones.

Active and selective catalysts for the hydrogenation of organic compounds and for the hydrogen peroxide synthesis are formed by means of one or more of the following preferred measures for the reaction of the above-described components with one another:

(1) The platinum metal complex, the complexing agent and the reducing agent are quickly, i.e. within less than 120 minutes, preferably within less than 30 minutes, brought to the reaction temperature in the essentially aqueous medium in the presence of the cleaned and preferably pickled support. The reaction temperature can be from room temperature to the boiling point of the aqueous solution, depending on the reaction mixture and the support. If the mixture tends to form smooth, relatively catalytically inactive coatings of palladium on the support at comparatively low temperatures of, for example, from 40 to 60° C., then a temperature which is at least 100° C. higher, but preferably at least 20° C. higher, should be chosen.

(2) A further measure according to the present invention is for the essentially aqueous mixture of all components to be heated for, for example, from about 5 to 600 minutes in the absence of the support before the support is brought into contact with the essentially aqueous solution of the reactants. This heating step requires less time, the higher the temperature selected and the stronger the reducing agent. In the system palladium chloride, ammonium chloride, ammonia is and hypophosphite, for example, from 30 to 90 minutes at from 60 to 90° C. is advantageous. If the solution is first heated in the absence of the support, it is also possible to choose a temperature at which a smooth coating would be formed on introduction of the support immediately after mixing all reactants.

(3) A further measure which leads to the formation of a supported catalyst according to the present invention in place of a support having a smooth coating is to increase the platinum metal salt concentration above that which forms a smooth layer by a factor of at least 2, i.e. for example from about 0.5 g/l of palladium in the case of a solution comprising palladium chloride, ammonia, ammonium chloride and a reducing agent to about 1–20 g/l.

(4) A further measure which leads to a catalyst according to the present invention is to mix all components with a previously prepared platinum metal sol (seed sol) shortly before, simultaneously with or shortly after dipping the support into the salt solution. Such a sol can be produced by known techniques, in the simplest case by mixing a platinum metal salt solution with a solution of sodium hypophosphite or another reducing agent in water. The amount of platinum metal employed as seed sol can be from 1 to 20% of the total amount, preferably from 5 to 15%.

(5) A further measure which can be employed according to the present invention is to destabilize the mixture of all dissolved components by using one or more of the complexing agents in a lower concentration than that required for the platinum metal complex solution to be stable toward the reducing agent at the reaction temperature selected. In the case of the solution of palladium chloride, ammonium chloride, ammonia and hypophosphite, the amount of concentrated ammonia required for a solution which is stable at 65° C. can, for example, be reduced from 100–160 ml/l to 75 ml/l or less in order to adapt the solution for the coating of the metallic support according to the present invention, i.e. to destabilize it.

(6) A further measure can be to destabilize the essentially aqueous solution of the platinum metal compound at a given temperature by increasing the concentration of the reducing agent and thus to prepare it for use according to the present invention. When palladium and a temperature of 60° C. are employed, the desired effect when using, for example, ammonium chloride and ammonia as complexing agents is achieved at >15 g/l of sodium hypophosphite as reducing agent.

In a preferred embodiment of the invention, catalytically active coatings are obtained by heating the reaction solution or the reaction mixture prior to the deposition. Heating is preferably carried out for from 5 to 600 minutes, in particular from 10 to 300 minutes and particularly preferably from 15 to 180 minutes. Here, the reaction solution or the reaction mixture, i.e. the aqueous medium containing platinum metal complex, reducing agent, base and complexing agent, is preferably brought to a temperature which is 30° C., preferably 20° C. and more preferably 15° C., above or below the desired reaction temperature for the deposition within less than 120 minutes, in particular within less than 60 minutes and preferably within less than 30 minutes, and is subsequently held at this temperature. The reaction solution or the reaction mixture is particularly preferably heated at a temperature which is up to 30° C., preferably up to 20° C., lower than the deposition temperature, or at about the desired deposition temperature. After the heating step, the metallic support is brought into contact with the reaction solution or the reaction mixture and, if necessary, the temperature of the reaction mixture is brought to a different temperature suitable for the deposition.

In a further embodiment of the process, the reaction solution or the reaction mixture is, if appropriate in addition to the heating procedure, admixed with a separately produced seed sol. Such a seed sol can be produced in a variety of ways (e.g. as described by Kosak, see above), most simply by mixing a platinum metal salt solution with a reducing agent in an aqueous medium. The addition of the seed sol should be carried out before, during or after bringing the metallic support into contact with the reaction solution or the reaction mixture. The amount of platinum metal used for producing a seed sol is preferably from 1 to 20% by weight, more preferably from 5 to 15% by weight, of the total amount of platinum metal used according to the present invention.

In the process of the present invention, it has been found to be advantageous to ensure sufficient circulation of the reaction solution or the reaction mixture, e.g. by pumping or stirring, during deposition of the platinum metal on the support.

The reaction time required for deposition of the platinum metal on the metallic supports is generally from 5 to 500 minutes, preferably from 10 to 300 minutes and particularly preferably from 15 to 120 minutes.

In the process of the present invention, preference is given to depositing more than 70% by weight, preferably more than 80% by weight and particularly preferably more than 90% by weight, of the platinum metals used on the metallic support. The platinum metal is generally bound so firmly to the metallic support that no appreciable detachment occurs as a result of contact with liquids and gases during use in catalytic reactions. Turbidity due to precipitation of the platinum metal is not observed.

Additional components, in particular the elements suitable as promoters or dopants, can, if desired, be introduced together with the platinum metal into the aqueous medium so that the deposition of the platinum metal and the incorporation of the additional components occurs essentially simultaneously. The addition of the additional components to the reaction solution can also be carried out toward the end or after the end of the platinum metal deposition, as a result of which the additional components are preferably incorporated at the surface of the active components. The additional components can also be applied in a separate second step to the catalysts of the present invention, e.g. by vapor deposition, preferably as described in EP-A-0 198 435, or by electroless or electrolytic deposition from aqueous and nonaqueous media. The application of additional components to the catalysts of the present invention in a separate second step is particularly advantageous when they are to be applied in a targeted manner to the surface of the active component. Moreover, deposition conditions different from the conditions employed according to the present invention can be chosen for the second step.

The catalysts obtained according to the present invention can subsequently be activated at from 0 to 500° C., preferably from 10 to 350° C., and pressures of from atmospheric pressure to a gauge pressure of 200 bar. Activation can be carried out, for example, in the presence of water and/or hydrogen, preferably hydrogen, at from 10 to 200° C., preferably from 30 to 150° C., and at atmospheric pressure or from 1 to 150 bar, preferably from 10 to 100 bar and particularly preferably from 30 to 70 bar. In general, activation takes from 0.1 to 10 hours, preferably from 1 to 5 hours. In a preferred embodiment of the process of the present invention, activation of the catalyst is carried out in the presence of the aqueous reaction medium described below for the synthesis of hydrogen peroxide according to the present invention.

In a preferred embodiment of the process of the present invention, the catalysts of the present invention are produced by dissolving at least 0.1–30 g/l, preferably 0.15–3 g/l and particularly preferably 0.15–0.5 g/l, of at least one platinum metal complex, if desired from 0.01 to 5 g/l, preferably from 0.01 to 0.5 g/l and preferably from 0.01 to 0.05 g/l, of at least one further element compound and, based on the platinum metal, at least 20, preferably 50 and particularly preferably at least 100, equivalents of a complexing agent and at least 10–100, preferably 20–80 and particularly preferably 40–60, equivalents of a reducing agent in an aqueous medium.

The present invention further provides a catalyst obtainable by one of the above-described methods.

The invention also provides platinum metal catalysts comprising a metallic support and a catalytically active coating applied thereto, wherein the catalytically active coating on the support surface comprises immobilized, discrete platinum metal particles having a mean particle diameter of less than about 1 µm, preferably less than about 100 nm. The platinum metal particles preferably have a mean diameter of more than about 1 nm and can, for example, have diameters in the range from about 20 to 100 nm. The discrete particles have an approximately spherical shape. In addition, the platinum metal particles essentially form a monolayer on the support, while prior art methods give nonuniform deposition, frequently in the form of mechanically unstable agglomerates.

In particular, the present invention provides a catalyst in which the metallic support consists essentially of steel, iron, copper, aluminum, silver, nickel, chromium, tungsten, titanium or a mixture and/or alloy thereof. Such catalysts preferably have a platinum metal content in the range from 0.01 to 50 g/kg of support. The catalysts obtainable by this process preferably display a selectivity of greater than 70%, in particular greater than 80% and particularly preferably greater than 85%, in the direct synthesis of hydrogen peroxide from the elements.

The catalysts of the present invention are eminently suitable for the hydrogenation of organic and inorganic compounds, in particular organic compounds such as olefins, e.g. ethylene, propylene, acetylene and butadiene, carbonyl compounds, e.g. aldehydes and ketones, and aromatics such as benzene, and particularly preferably for the hydrogenation of oxygen.

The present invention further provides a process for preparing hydrogen peroxide in which a catalyst as described above in an essentially aqueous solution is brought into contact with an oxygen/hydrogen mixture having a mixing ratio in the range from 4:1 to 30:1.

The present invention likewise provides for the use of the catalysts of the present invention for the synthesis of hydrogen peroxide from the elements, both by the anthraquinone process or an analogous process and by direct synthesis, i.e. direct reaction of oxygen and hydrogen over a platinum metal catalyst in a liquid or gaseous medium, preferably by one of the methods described above. Suitable processes are, for example, described in WO 98/16463. The use of the catalysts of the present invention for the direct synthesis of $H_2O_2$ is particularly preferred.

Suitable reactors for the synthesis of $H_2O_2$ are described, for example, in EP-A-068 862, EP-A-201 614 and EP-A-448 884. Particular preference is given to tube reactors fitted with cylindrical catalyst units, since this enables uniform flow which allows particularly good reaction conditions. Tube reactors containing beds of shaped catalyst bodies, e.g. mesh rings, are also suitable.

The reaction is generally carried out using a flooded reactor. As reaction medium, preference is given to water and/or $C_1$–$C_3$-alkanols, in particular water and/or methanol. If water is used as reaction medium, up to 20% by weight of the alcohol, preferably methanol, can be added thereto. If an alcoholic reaction medium is used, it can contain up to 40% by weight, preferably up to 20% by weight and particularly preferably up to 5% by weight, of water. Very particular preference is given to using water as sole reaction medium. To stabilize the hydrogen peroxide against decomposition, acids whose pKa is preferably less than that of acetic acid, in particular mineral acids such as sulfuric acid, phosphoric acid or hydrochloric acid, are added to the reaction medium. The acid concentration is generally at least $10^{-4}$ mol/liter, preferably from $10^{-3}$ to $10^{-1}$ mol/liter. In addition, traces of bromide or chloride in concentrations of from 1 to 1000 ppm, preferably from 5 to 700 ppm and particularly preferably from 50 to 600 ppm, are generally added. However, it is also possible to use other stabilizers such as formaldehyde.

The reaction gas, which may comprise not only hydrogen and oxygen but also inert gases such as nitrogen or noble gases, generally has an $O_2$:$H_2$ ratio in the range from 2:1 to 1000:1. Preference is given to molar ratios in the range from 5:1 to 100:1, in particular from 4:1 to 60:1 and particularly preferably from 20:1 to 50:1. The oxygen used in the reaction gas can also be mixed into the reaction gas in the form of air.

In a preferred embodiment, the reaction gas is circulated. In this case, the molar ratio in the fresh gas mixture is close to the stoichiometric ratio, preferably in the range from 1.5:1 to 0.5:1. The molar ratio of $O_2$:$H_2$ in the circulating gas should be in the range from 5:1 to 1000:1, preferably in the range from 20:1 to 100:1. The reaction can be carried out either at atmospheric pressure or at gauge pressures of up to 200 bar. The pressure is preferably in the range from 10 to 300 bar, in particular from 10 to 80 bar. The reaction temperature can be in the range from 0 to 60° C., preferably in the range from 5 to 60° C. and in particular from 15 to 45° C. The partial pressures of the reaction gases in the reaction gas mixture both in the reactor and in the circulating gas are preferably chosen so that the hydrogen concentration is below the lower explosive limit under reaction conditions.

Reaction gas and reaction medium can be passed through the reactor in cocurrent or in countercurrent to one another, preferably in cocurrent, with the liquid phase forming the continuous phase and the reaction gas forming the discontinuous phase. In the preferred vertical reactor construction (upright reactor), reaction gas and reaction medium are preferably passed through the reactor in countercurrent from the bottom to the top. Here, hydrogen can be fed into the reactor via one or more intermediate feed points downstream of the feed point for oxygen or air. The empty tube velocity of reaction gas and reaction medium is in the range from 50 to 1000 m/h., preferably in the range from 150 to 300 m/h.

The process described enables hydrogen peroxide solutions having hydrogen peroxide contents above 2% by weight, preferably in the range from 3 to 25% by weight, to be prepared. The concentration can be preselected in the desired manner by adjustment of the material flows. The selectivity of hydrogen peroxide formation is, for example, above 65%, preferably ≧70%. Long-term tests have shown that there is no decrease, or only a slight decrease, in the catalyst activity and selectivity even after an operating time of more than 40 days.

The present invention is illustrated by the following examples, without being restricted thereby.

EXAMPLES

Production of Catalyst Supports

I.a Production of Monoliths from Woven Stainless Steel Mesh

One corrugated and one smooth mesh made of stainless steel (material No. 1.4539, mesh opening 200 µm, wire diameter 140 µm) were placed on top of one another and rolled to form a cylindrical monolith having a height of 5 cm and a diameter of likewise 5 cm in such a way that an axial hollow space having a diameter of 16 mm was formed in the center. The ends of the meshes were fixed by point welding.

The mesh plane spacing of the smooth mesh was at least 1 mm. The monolith obtained was treated in succession with ethyl acetate, acetone and distilled water in an ultrasonic bath and was subsequently dried.

I.b Pretreatment of the Monolith

The monolith produced and cleaned as described under I.a was treated with concentrated hydrochloric acid (37% strength) at 60° C. for 180 minutes and subsequently rinsed a number of times with distilled water.

I.c Production of Wire Mesh Rings of Woven Stainless Steel Mesh

Two strips of stainless steel mesh (material No. 1.4539, mesh opening 150 μm, wire diameter 100 μm) having dimensions of 17×3 mm were placed on top of one another and shaped to form wire mesh rings having a diameter of 3 mm and a height of 3 mm. 45 g (approximately 77 ml) of the wire mesh rings were in each case treated in succession with ethyl acetate, acetone and distilled water in an ultrasonic bath and were subsequently dried.

I.d Pretreatment of the Wire Mesh Rings

The wire mesh rings produced as described under I.c were treated with concentrated hydrochloric acid (37% strength) at 60° C. for 60 minutes and subsequently rinsed a number of times with distilled water.

The results of the use testing of the catalysts CC1, CC2 and IC1 to IC12 in the direct synthesis of hydrogen peroxide are summarized in Table 1.

II. Production of the Catalysts CC1 and CC2 Which are not According to the Present Invention

CC1:

In a 2000 ml glass beaker, 1500 ml of deionized water were heated to 70° C. and admixed with an aqueous solution of $Na_2PdCl_4$ (40 g; 1% strength solution, based on the palladium content). Subsequently, a monolith produced as described under I.b was hung into the glass beaker. While stirring, 20 g of a 0.83% strength aqueous solution of $NaH_2PO_2$ was subsequently added and the reaction mixture was heated to 80–88° C. The reaction mixture became turbid and acquired a dark color. The reaction mixture was stirred for a further 90 minutes at this temperature. During this time, the solution decolorized and became clear again. The monolith, which had become dark gray, was then taken from the reaction mixture and rinsed with water, which resulted in a fine black solid becoming detached. To determine the amount of palladium metal deposited, the washing liquid was combined with the solid and the reaction mixture, the insoluble constituents were brought into solution using aqua regia and the palladium content of the resulting solution was subsequently determined. Deposition of 44% of the available palladium on the monolith could be calculated from these data.

CC2:

A monolith produced as described in I.b was hung into a glass beaker in such a way that it was completely covered by reaction solution added subsequently. A solution of 9.6 g of $NaH_2PO_2.1 H_2O$, 21.6 g of ammonium chloride and 134 ml of ammonia solution (25% strength) were then added while stirring to 180 ml of deionized water and 19.06 g of an aqueous solution of $Na_2PdCl_4$ (1% strength, based on the palladium content) were added thereto, the reaction solution was heated stepwise to 65° C. over a period of 2 hours while stirring and the mixture was stirred for 60 minutes at this temperature. The monolith was then taken from the reaction solution and rinsed with water. No solid was detached from the support during this procedure. The reaction solution was subsequently combined with the washing solution and the palladium content of the combined solutions was determined. Deposition of >99% of the available palladium on the monolith could be calculated from these data.

III. Production of the Catalysts IC1 to IC12 According to the Present Invention

IC1:

A solution of 9.6 g of $NaH_2PO_2.1 H_2O$, 21.6 g of ammonium chloride and 134 ml of aqueous ammonia solution (25% strength) in 660 ml of deionized water was made up in a 1000 ml glass beaker. Subsequently, 24.12 g of aqueous $Na_2PdCl_4$ solution (1% strength, based on the palladium content) was added thereto while stirring, the solution was heated to 75° C. and was stirred at this temperature for 60 minutes. The solution remained colorless and clear for the whole time. Subsequently, a monolith produced as described in I.b was hung into the reaction solution and the reaction mixture was stirred for a further 65 minutes at 75° C. The reaction solution remained colorless and clear for the whole time. The monolith was then taken out and rinsed with water. No solid was detached from the support during this procedure. Reaction solution and washing solution were subsequently combined and the palladium content of the solution was determined. Deposition of 99% of the available palladium on the monolith could be calculated from these data.

IC2:

A solution of 9.6 g of $NaH_2PO_2.1 H_2O$, 21.6 g of ammonium chloride and 134 ml of aqueous ammonia solution (25% strength) in 560 ml of deionized water was made up in a 1000 ml glass beaker. Subsequently, 41.4 mg of lead(II) nitrate, dissolved in 100 ml of water, and 24.12 g of an aqueous $Na_2PdCl_4$ solution (1% strength, based on the palladium content) was added thereto while stirring, the mixture was heated to 65° C. and stirred at this temperature for a further 60 minutes. Subsequently, a monolith produced as described in I.b was hung into the solution, the reaction mixture was heated to 75° C. and was subsequently stirred for a further 210 minutes at this temperature. The reaction solution remained colorless and clear for the whole time. The monolith was then taken from the reaction mixture and rinsed with water. No precipitate was detached from the support during this procedure. Reaction solution and washing solution were subsequently combined and the palladium content of the combined solution was determined. Deposition of more than 99% of the available palladium on the monolith could be calculated from these data.

IC3:

A solution of 9.6 g of $NaH_2PO_2.1 H_2O$, 21.6 g of ammonium chloride and 134 ml of aqueous ammonia solution (25% strength) in 560 ml of deionized water was made up in a 1000 ml glass beaker. Subsequently, 55 mg of $(NH_4)_2IrCl_6$, dissolved in 100 ml of water, and 24.12 g of an aqueous $Na_2PdCl_4$ solution (1% strength, based on the palladium content) was added thereto while stirring, the mixture was heated to 65° C. and stirred at this temperature for a further 60 minutes. Subsequently, a monolith produced as described in I.b was hung into the solution, the reaction mixture was heated to 75° C. and was stirred for a further 170 minutes at this temperature. The reaction solution remained colorless and clear for the whole time. The monolith was then taken from the reaction mixture and rinsed with water. No solid was detached from the support during this procedure. Reaction solution and washing solution were subsequently combined and the palladium content of the combined solution was determined. Deposition of 96% of the available palladium on the monolith could be calculated from these data.

IC4:

A solution of 9.6 g of $NaH_2PO_2 \cdot 1\ H_2O$, 10 g of ethylenediaminetetraacetic acid tetrasodium salt and 134 ml of aqueous ammonia solution (25% strength) in 650 ml of deionized water was made up in a 1000 ml glass beaker. Subsequently, 24.12 g of an aqueous $Na_2PdCl_4$ solution (1% strength, based on the palladium content) was added thereto while stirring, the reaction solution was heated to 75° C. and stirred at this temperature for a further 60 minutes. Subsequently, a monolith produced as described in I.b was hung into the solution, the reaction mixture was heated to 75° C. and was stirred for a further 40 minutes at 75° C. The aqueous solution remained colorless and clear for the whole time. The monolith was then taken from the reaction mixture and rinsed with water. No solid was detached from the support during this procedure. Reaction solution and washing solution were subsequently combined and the palladium content of the combined solution was determined. Deposition of 96.4% of the available palladium on the monolith could be calculated from these data.

IC5:

A solution of 9.6 g of $NaH_2PO_2 \cdot 1\ H_2O$, 21.6 g of ammonium chloride and 134 ml of aqueous ammonia solution (25% strength) in 560 ml of deionized water was made up in a 1000 ml round-bottomed flask fitted with a Teflon blade stirrer. Subsequently, 24.12 g of an aqueous $Na_2PdCl_4$ solution (1% strength, based on the palladium content) was added thereto while stirring, the reaction solution was heated to 75° C. and stirred at this temperature for a further 60 minutes. 45 g of the wire mesh rings produced as described in I.d were subsequently added to the reaction solution and the reaction mixture was stirred for a further 180 minutes at 75° C. The reaction solution remained colorless and clear for the whole time. The wire mesh rings were then separated from the reaction solution and rinsed with water. No solid was detached from the rings during this procedure. Reaction solution and washing solution were subsequently combined and the palladium content of the combined solution was determined. Deposition of more than 99.5% of the available palladium on the rings could be calculated from these data.

IC6:

A solution of 19.2 g of $NaH_2PO_2 \cdot 1\ H_2O$, 43.2 g of ammonium chloride and 268 ml of aqueous ammonia solution (25% strength) in 1320 ml of deionized water was made up in a 2000 ml round-bottomed flask fitted with a Teflon blade stirrer. 48.24 g of an aqueous $Na_2PdCl_4$ solution (1% strength, based on the palladium content) was added thereto while stirring, the reaction solution was heated to 75° C. and stirred at this temperature for a further 40 minutes. 45 g of the wire mesh rings produced as described in I.d were subsequently added to the reaction-solution and the reaction solution was stirred for a further 180 minutes at a temperature in the range from 75° C. to 80° C. The reaction solution remained colorless and clear for the whole time. The wire mesh rings were then separated from the reaction solution and rinsed with water. No solid was detached from the rings during this procedure. Reaction solution and washing solution were subsequently combined and the palladium content of the combined solution was determined. Deposition of more than 99% of the available palladium on the rings could be calculated from these data.

IC7:

A first solution of 8.64 g of $NaH_2PO_2 \cdot 1\ H_2O$, 19.4 g of ammonium chloride, 121 ml of aqueous ammonia solution (25% strength) and 19.5 g of an aqueous $Na_2PdCl_4$ solution (1% strength, based on the palladium content) in 594 ml of deionized water was made up in a 1000 ml round-bottomed flask fitted with a Teflon blade stirrer. A second solution comprising 1.224 g of $NaH_2PO_2 \cdot 1\ H_2O$, dissolved in 80 ml of water, and 4.62 g of an aqueous $Na_2PdCl_4$ solution (1% strength, based on the palladium content) was made up in a 100 ml round-bottomed flask. The second solution was allowed to stand until it began to change color to brown and immediately after the commencement of the color change to brown was added dropwise to the first solution over a period of 5 minutes. The reaction mixture obtained was subsequently heated to 40–45° C. while stirring. After 20 minutes at this temperature, 45 g of the wire mesh rings produced as described in I.d were added to the now colorless and clear reaction solution and the reaction mixture was heated to 75° C. over a period of 30 minutes. The wire mesh rings were then separated from the reaction solution and rinsed with water. A small amount of black precipitate remained in the reaction solution. Reaction solution together with solid and washing solution were subsequently combined, the solid was brought into solution using aqua regia and the palladium content of the resulting solution was determined. Deposition of more than 89% of the available palladium on the supports could be calculated from these data.

IC8:

A solution of 9.6 g of $NaH_2PO_2 \cdot 1\ H_2O$, 21.6 g of ammonium chloride and 32.4 ml of aqueous ammonia solution (25% strength) in 160 ml of deionized water was made up in a 1000 ml round-bottomed flask fitted with a Teflon blade stirrer. 24.12 g of an aqueous $Na_2PdCl_4$ solution and 0.24 g of an aqueous $H_2PtCl_4$ solution (each 1% strength, based on the palladium or platinum content) were added thereto while stirring, the reaction solution was heated to 75° C. and stirred for a further 20 minutes at this temperature. 45 g of the wire mesh rings produced as described in I.d were subsequently added to the reaction solution and the reaction mixture was stirred for a further 120 minutes at 75° C. The reaction solution remained colorless and clear for the whole time. The wire mesh rings were then separated from the reaction solution and rinsed with water. No solid was detached from the supports during this procedure. Reaction solution and washing solution were subsequently combined and the palladium and platinum contents were determined. Deposition of 87% of the available palladium and 58% of the available platinum on the supports could be calculated from these data.

IC9:

A solution of 9.6 g of $NaH_2PO_2 \cdot 1\ H_2O$, 21.6 g of ammonium chloride and 134 ml of aqueous ammonia solution (25% strength) in 660 ml of deionized water was made up in a 1000 ml round-bottomed flask fitted with a Teflon blade stirrer. 24.12 g of an aqueous $Na_2PdCl_4$ solution (1% strength, based on the palladium content) were added thereto, the solution was heated while stirring to 75° C. and was stirred for a further 25 minutes at this temperature. 45 g of the wire mesh rings produced as described in I.c were subsequently added to the reaction solution and the reaction mixture was stirred for a further 120 minutes at 75° C. The reaction solution remained colorless and clear for the whole time. The wire mesh rings were then separated from the reaction solution and rinsed with water. No solid was detached from the supports during this procedure. Reaction solution and washing solution were subsequently combined and the palladium content of the combined solution was determined. Deposition of 84.6% of the available palladium on the supports could be calculated from these data.

IC10:

45 g of the wire mesh rings produced as described in I.d were introduced into a cylindrical 2 l vessel provided with heating mantel and circulation pump, and a solution of 9.6 g of $NaH_2PO_2.1\ H_2O$, 21.6 g of ammonium chloride and 32 ml of an aqueous ammonia solution (25% strength) in 160 ml of deionized water was added. The reaction mixture was heated to 56° C. 12.06 g of an aqueous $Na_2PdCl_4$ solution (1% strength, based on the palladium content) and 0.12 g of an aqueous $H_2PtCl_4$ solution (1% strength, based on the platinum content) were subsequently added thereto and the reaction mixture was heated to 68° C. over a period of 40 minutes while circulating the solution. The aqueous solution remained colorless and clear for the whole time. The wire mesh rings were then separated from the reaction solution and rinsed with water. No solid was detached from the supports during this procedure. Reaction solution and washing solution were subsequently combined and the palladium content of the combined solution was determined. Deposition of 90% of the available palladium on the supports could be calculated from these data.

IC11:

A solution of 99.7 g of $NaH_2PO_2.1\ H_2O$, 224.4 g of ammonium chloride and 337 ml of aqueous ammonia solution (25% strength) in 1663 ml of deionized water was made up in a cylindrical 2 l vessel provided with heating mantel and circulation pump. 250.6 g of an aqueous $Na_2PdCl_4$ solution (1% strength, based on the palladium content) were added thereto, and the reaction solution was heated to 58° C. over a period of 25 minutes while maintaining circulation. 468 g of the wire mesh rings produced as described in I.d were then added and the reaction mixture was heated to 70° C. and circulated for a further 25 minutes. The aqueous solution remained colorless and clear for the whole time. The wire mesh rings were then separated from the reaction solution and rinsed with water. No solid was detached from the supports during this procedure. Reaction solution and washing solution were subsequently combined and the palladium content of the combined solution was determined. Deposition of 96% of the available palladium on the supports could be calculated from these data.

IC12:

468 g of the wire mesh rings produced as described in I.d were introduced into a cylindrical 2 l vessel provided with heating mantel and circulation pump, and a solution, which had been heated to 45° C., of 99.7 g of $NaH_2PO_2.1\ H_2O$, 224.4 g of ammonium chloride, 337 ml of an aqueous ammonia solution (25% strength) and 250.6 g of an aqueous $Na_2PdCl_4$ solution (1% strength, based on the palladium content) in 1663 ml of deionized water was subsequently added. The reaction mixture was then heated to 80° C. over a period of 120 minutes while maintaining circulation. Vigorous gas evolution was observed above a temperature of about 56° C., but this steadily decreased with increasing reaction time and was virtually complete by the end of the time. The aqueous solution remained colorless and clear for the whole time. The wire mesh rings were then separated from the reaction solution and rinsed with water. No solid was detached from the supports during this procedure. Reaction solution and washing solution were subsequently combined and the palladium content of the combined solution was determined. Deposition of 99% of the available palladium on the supports could be calculated from these data.

All the catalysts obtained (CC1, CC2, IC1 to IC12) were treated with hydrogen for 3 hours at 65° C. and 50 bar pressure prior to testing of the use properties.

IV. Testing of the use Properties

The properties of the catalysts obtained were tested in the direct synthesis of hydrogen peroxide from hydrogen and oxygen (Examples E1 to E14) and in the case of IC11 also in the hydrogenation of acetophenone (Example E15).

For this purpose, the catalysts CC1 and CC2 which were not according to the present invention (Comparative Examples CE1 and CE2 in Table 1) and the catalysts IC1 to IC4 according to the present invention (Examples E1 to E5 according to the present invention in Table 1) were employed in a 300 ml autoclave fitted with stirrer, thermostatic control and pressure maintenance at 50 bar as reaction vessel. In this autoclave, a catalyst monolith was in each case installed centered about the stirrer axis so that it was supplied uniformly with liquid and gas by the stirrer. Feed lines for oxygen, hydrogen and the reaction medium were located in the bottom of the autoclave. A discharge line through which the product/gas mixture could be taken continuously was located in the autoclave lid. After subtracting the volumes for all internal fittings, an effective reaction volume of 200 ml was available. The reaction medium employed was water containing 544 ppm of hydrogen bromide and 1200 ppm of phosphoric acid. The autoclave was flooded with the reaction medium and closed. Subsequently, the autoclave was heated and the reaction medium, oxygen and hydrogen were passed continuously through the reaction vessel at constant flow rates. The hydrogen content in the outflowing gas was determined by means of a thermal conductivity detector. The $H_2O_2$ content of the liquid output was determined by titration. The selectivity to hydrogen peroxide was based on the hydrogen consumed in the reactor.

For Examples E6 to E12 according to the present invention, use was made of the above-described autoclave but it was provided with a metal basket for accommodating the catalysts IC5 to IC10 (wire mesh rings); this basket was fastened to the lid of the autoclave. In its center, the basket had a cylindrical opening for the shaft of the stirrer, so that the respective catalyst was supplied uniformly with liquid and gas. The reaction medium employed was water having a hydrogen bromide content of 121 ppm and a phosphoric acid content of 5000 ppm. The reaction vessel was flooded with the reaction medium and closed. Subsequently, a constant stream of reaction medium, hydrogen and oxygen was passed through the reactor. The product/gas mixture was continuously taken off at the autoclave lid.

The reaction conditions and results of the reaction are summarized in Table 1.

The reaction temperature T, the total reaction time $t_1$ and the time $t_2$ after which the hydrogen conversion and the hydrogen peroxide output was constant are likewise indicated in Table 1.

In Examples E13 and E14:

A double-wall metal tube reactor having an internal diameter of 2.2 cm and a length of 2.00 m was charged with the catalyst (E13: IC11; E14: IC12). The tube reactor charged with the catalyst was connected to a circulation pump for the gas circuit and to a cooling/heating circuit. Subsequently, the apparatus was filled with a solution of 121 ppm of hydrogen bromide and 5000 ppm of phosphoric acid in water as reaction medium and was closed. The reaction medium was passed through the apparatus at a constant flow rate of 500 ml/h. The entire plant was set to a pressure of 50 bar by supply of nitrogen using a pressure maintenance valve. The gas circulation (E13: 2500 standard l/h; E14: 15,600 standard l/h) was set by means of the gas circulation pump. The nitrogen in the gas circuit was subsequently replaced by a mixture of oxgyen and hydrogen, with the ratio of the two gases being set to a hydrogen content of 3%. A constant stream of 44 standard 1 of circulating gas/h was branched off from the gas circuit and passed to a thermal conductivity detector to determine the hydrogen content of the waste gas. The feed rates of hydrogen and oxygen were regulated by means of mass flow meters. During the reaction, the amounts of fresh gas and waste gas were continually recorded. The reaction medium leaving the reactor was separated from the circulating gas in a separator and conveyed out of the plant. The hydrogen peroxide content in the reaction medium separated off was continually monitored by titration with $KMnO_4$.

TABLE 1

| Ex. | Catalyst monolith = (M) Rings = (R) | HBr [ppm] | $H_3PO_4$ [ppm] | Flow rate Reaction medium [ml/h] | Gas stream [standard l/h] | Ratio $O_2:H_2$ | T [° C.] | $t_1$[a]; $t_2$[b] [h] | Conversion of $H_2$ [%] | $H_2O_2$ content [%] | Selectivity [%] |
|---|---|---|---|---|---|---|---|---|---|---|---|
| CE1 | CC1(M) | 544 | 1200 | 270 | 324 | 9:1 | 21 | 21; 12 | 23.5 | 3.0 | 70 |
| CE2 | CC1(M) | 544 | 1200 | 270 | 324 | 9:1 | 40 | ?;? | 24.6 | 3.2 | 70 |
| CE3 | CC2(M) | 544 | 1200 | 270 | 324 | 9:1 | 19 | 15; 10 | 6.0 | 0.4 | 36 |
| E1 | IC1(M) | 544 | 1200 | 268 | 324 | 9:1 | 39 | 11; 8 | 21.0 | 3.2 | 85 |
| E2 | IC1(M) | 544 | 1200 | 35 | 335 | 9.6:0.4 | 41 | ?; 36 | 20.0 | 8.7 | 82 |
| E3 | IC2(M) | 544 | 1200 | 264 | 324 | 9:1 | 38 | 11; 8 | 28.0 | 3.4 | 68 |
| E4 | IC3(M) | 544 | 1200 | 62 | 324 | 9:1 | 21 | 28; 21 | 24.0 | 8.5 | 51 |
| E5 | IC4(M) | 544 | 1200 | 262 | 324 | 9:1 | 35 | 17; 13 | 18.0 | 2.7 | 80 |
| E6 | IC5(R) | 121 | 5000 | 41 | 324 | 9.6:0.4 | 44 | 50; 40 | 14.0 | 5.7 | 84 |
| E7 | IC6(R) | 121 | 5000 | 42 | 324 | 9.6:0.4 | 40 | 25; 20 | 14.0 | 5.9 | 90 |
| E8 | IC7(R) | 121 | 5000 | 77 | 324 | 9.6:0.4 | 40 | 19; 11 | 17.0 | 3.4 | 77 |
| E9 | IC7(R) | 121 | 5000 | 51 | 469 | 9.6:0.4 | 40 | 17; 12 | 10.5 | 6.2 | 100 |
| E10 | IC8(R) | 121 | 5000 | 78 | 469 | 9.6:0.4 | 33 | 14; 10 | 9.1 | 3.3 | 100 |
| E11 | IC9(R) | 121 | 5000 | 78 | 469 | 9.6:0.4 | 39 | 17; 14 | 16.9 | 2.3 | 52 |
| E12 | IC10(R) | 121 | 5000 | 78 | 222 | 10:1 | 40 | 19; 24 | 31.6 | 8.1 | 57 |
| E13 | IC11(R) | 121 | 5000 | 500 | 2500 | 9.7:0.3 | 39 | 22; 17 | 96 | 3.6 | 65 |
| E14 | IC12(R) | 121 | 5000 | 500 | 15600 | 9.7:0.3 | 40 | 11; 8 | 96 | 6.6 | 67 |

[a]Total reaction time
[b]Time after which the H2 conversion was constant

Example E15:

For Example E15 according to the present invention, the above-described 300 ml autoclave provided with a metal basket fastened to the lid of the autoclave, as used in Example E6 to E12, was employed; in the present example, the metal basket was used for accommodating 9.2 g of the catalyst IC11 (wire mesh rings). In its center, the basket had a cylindrical opening for the shaft of the stirrer, so that the catalyst was supplied uniformly with liquid and gas. The autoclave was charged with 200 ml of cylcohexane and 8 g of acetophenone, closed and freed of air by pressurizing it twice to 100 bar with nitrogen. The autoclave was subsequently heated to 120° C. and 250 bar of hydrogen were injected. While injecting further hydrogen to replace that consumed, the mixture was stirred for a further 60 minutes at this temperature. A total of 1.59 liters of hydrogen were consumed. Analysis of the resulting product by gas chromatography indicated complete conversion of the acetophenone to form 1-phenylethanol (81%) and ethylbenzene (19%).

We claim:

1. A process for producing catalysts by electroless deposition of at least one platinum metal on a metallic support, in which an aqueous medium which comprises at least one platinum metal complex, at least one reducing agent and at least one complexing agent and has a pH of more than 4 is brought into contact with the metallic support to deposit the platinum metal, wherein the deposition of the platinum metal occurs in the form of discrete, immobilized particles from essentially homogeneous aqueous solution.

2. A process as claimed in claim 1, wherein from about 1 to 1000 equivalents of complexing agent, based on the platinum metal, are present in the solution.

3. A process as claimed in claim 1, wherein the reducing agent is used in a 10- to 100-fold molar excess, based on the platinum metal.

4. A process as claimed in claim 1, wherein the deposition is carried out at a reaction temperature in the range from 40 to 85° C.

5. A process as claimed in claim 1, wherein the pH is set by means of at least one base selected from the group consisting of ammonia, primary, secondary and tertiary amines, alkali metal and alkaline earth metal hydroxides and alkali metal and alkaline earth metal carbonates.

6. A process as claimed in claim 1, wherein the complex of the platinum metal has a complex formation constant of $\geq 1000$.

7. A process as claimed in claim 1, wherein the platinum metal comprises from 80 to 100% by weight of palladium and from 0 to 20% by weight of platinum or iridium.

8. A process as claimed in claim 1, wherein at least 0.1–30 g/l of at least one platinum complex, optionally from 0.001 to 5 g/l of at least one further element compound and, based on the noble metal, at least 20 equivalents of a complexing agent and at least 10–100 equivalents of a reducing agent are dissolved in an aqueous medium.

9. A process as claimed in claim 1, comprising at least one of the following measures:
    (1) heating the aqueous medium to the reaction temperature over a period of less than about 120 minutes and in the presence of the metallic support;
    (2) heating the aqueous medium in the absence of the metallic support;
    (3) increasing the noble metal ion concentration in the aqueous medium to above the level customary for smooth coatings;
    (4) adding a noble metal seed sol to the aqueous medium;
    (5) destabilizing the noble metal complex by reducing the concentration of complexing agent in the aqueous medium; or
    (6) destabilizing the noble metal complex by increasing the concentration of reducing agent.

10. The process according to claim 1, wherein the pH is 8 to 12.

11. A process comprising hydrogenating an organic compound with the catalyst obtained by the process of claim 1.

12. A process for preparing hydrogen peroxide by direct synthesis, which comprises bringing a catalyst obtained by the process of claim 1 into contact with an oxygen/hydrogen mixture having a mixing ratio in the range from about 5:1 to 100:1.

13. A process as claimed in claim 12, wherein the catalyst and the oxygen/hydrogen mixture are brought into contact at from about 10 to 60° C. and a pressure in the range from about 10 to 300 bar.

14. A process as claimed in claim 12, wherein from about 200 to 7500 ppm of at least one acid are added to the aqueous solution.

15. A process comprising hydrogenating an organic compound with a catalyst comprising a metallic support and a catalytically active coating applied hereto, wherein the catalytically active coating on the support surface comprises immobilized, discrete noble metal of transition group VIII of the Periodic Table particles having a mean particle diameter of less than about 1 $\mu$m.

16. A process for preparing hydrogen peroxide by direct synthesis, which comprises bringing a catalyst comprising a metallic support and a catalytically active coating applied hereto, wherein the catalytically active coating on the support surface comprises immobilized, discrete noble metal of transition group VIII of the Periodic Table particles having a mean particle diameter of less than about 1 $\mu$m into contact with an oxygen/hydrogen mixture having a mixing ratio in the range from about 5:1 to 100:1.

17. A process as claimed in claim 16, wherein the catalyst and the oxygen/hydrogen mixture are brought into contact at from about 10 to 60° C. and a pressure in the range from about 10 to 300 bar.

18. A process as claimed in claim 16, wherein from about 200 to 7500 ppm of at least one acid are added to the aqueous solution.

* * * * *